(12) United States Patent
Linton

(10) Patent No.: US 11,839,707 B2
(45) Date of Patent: *Dec. 12, 2023

(54) BREATHING MASK

(71) Applicant: Jennifer A. Linton, Dover, DE (US)

(72) Inventor: Jennifer A. Linton, Dover, DE (US)

(*) Notice: Subject to any disclaimer, the term of this patent is extended or adjusted under 35 U.S.C. 154(b) by 655 days.

This patent is subject to a terminal disclaimer.

(21) Appl. No.: 16/782,333

(22) Filed: Feb. 5, 2020

(65) Prior Publication Data

US 2020/0171296 A1 Jun. 4, 2020

Related U.S. Application Data

(63) Continuation of application No. 15/416,224, filed on Jan. 26, 2017, now Pat. No. 10,589,079.

(Continued)

(51) Int. Cl.
| | |
|---|---|
| *A61M 16/06* | (2006.01) |
| *A61M 39/12* | (2006.01) |
| *A61M 39/10* | (2006.01) |
| *A61M 39/24* | (2006.01) |
| *A61M 16/08* | (2006.01) |

(52) U.S. Cl.
CPC ........ *A61M 39/12* (2013.01); *A61M 16/0605* (2014.02); *A61M 16/0683* (2013.01); *A61M 16/085* (2014.02); *A61M 16/0841* (2014.02); *A61M 39/1011* (2013.01); *A61M 39/24* (2013.01); *A61M 2039/2426* (2013.01)

(58) Field of Classification Search
CPC ............ A61M 16/085; A61M 16/0841; A61M 39/1011; A61M 2016/0661; A61M 16/0633
See application file for complete search history.

(56) References Cited

U.S. PATENT DOCUMENTS

| | | | | |
|---|---|---|---|---|
| 2,625,155 A | * | 1/1953 | Engelder | A61M 16/06 D24/110.4 |
| 2,859,748 A | | 11/1958 | Hudson | |

(Continued)

FOREIGN PATENT DOCUMENTS

| | | |
|---|---|---|
| CN | 2829768 Y | 10/2006 |
| CN | 201006137 Y | 1/2008 |

(Continued)

OTHER PUBLICATIONS

Chinese Office Action dated Sep. 9, 2021, in connection with corresponding CN Application No. 201780008575.X (19 pp., including machine-generated English translation).

(Continued)

*Primary Examiner* — Nathan R Price
*Assistant Examiner* — Courtney B Fredrickson
(74) *Attorney, Agent, or Firm* — Maier & Maier, PLLC

(57) ABSTRACT

A breathing mask which is convenient for enteral nutrition using a nasogastric feeding tube when the mask is in use may be provided. The breathing mask may include at least one nasogastric tube port. The port may allow a nasogastric tube to pass through the mask without substantially affecting the seal or pressure of the mask while accommodating enteral feeding. In addition, the breathing mask may incarnate the human-centered design to reduce discomfort in patients and is favorable for therapy and rehabilitation.

16 Claims, 12 Drawing Sheets

Related U.S. Application Data

(60) Provisional application No. 62/287,625, filed on Jan. 27, 2016.

(56) References Cited

U.S. PATENT DOCUMENTS

| | | | |
|---|---|---|---|
| 3,786,809 A * | 1/1974 | Kitrilakis | A61M 16/0627 128/205.26 |
| 3,827,433 A | 8/1974 | Shannon | |
| 5,465,712 A | 11/1995 | Malis | |
| 6,615,829 B2 | 9/2003 | Horn et al. | |
| 6,631,713 B1 | 10/2003 | Christopher | |
| 6,932,239 B2 | 8/2005 | McKitrick | |
| 8,365,734 B1 | 2/2013 | Lehman | |
| 8,915,250 B2 | 12/2014 | Dugan et al. | |
| 2002/0170557 A1 | 11/2002 | Schmidt | |
| 2003/0024530 A1 | 2/2003 | Sniadach | |
| 2003/0024533 A1 * | 2/2003 | Sniadach | A61M 16/06 128/202.28 |
| 2005/0098183 A1 | 5/2005 | Nash et al. | |
| 2006/0054168 A1 | 3/2006 | Yu | |
| 2006/0249160 A1 | 11/2006 | Scarberry et al. | |
| 2008/0011295 A1 | 1/2008 | Mueller | |
| 2008/0142003 A1 * | 6/2008 | Depel | A61M 16/0484 128/200.24 |
| 2010/0116276 A1 | 5/2010 | Bayasi | |
| 2011/0130650 A1 | 6/2011 | Dayan et al. | |
| 2012/0289851 A1 * | 11/2012 | Varga | A61B 5/097 600/532 |
| 2012/0330111 A1 * | 12/2012 | Borody | A61M 16/0488 600/300 |
| 2013/0152936 A1 * | 6/2013 | Ho | F16L 3/13 128/205.25 |
| 2014/0090643 A1 | 4/2014 | Stallard et al. | |
| 2014/0261431 A1 | 9/2014 | Murphy | |
| 2015/0122254 A1 | 5/2015 | Henry | |
| 2015/0165150 A1 | 6/2015 | Quinn et al. | |
| 2015/0335873 A1 | 11/2015 | Khalaj | |
| 2016/0008566 A1 * | 1/2016 | Partington | A61M 16/0875 128/205.12 |

FOREIGN PATENT DOCUMENTS

| | | |
|---|---|---|
| CN | 201175514 Y | 1/2009 |
| CN | 201684263 U | 12/2010 |
| CN | 102019023 A | 4/2011 |
| CN | 202036653 U | 11/2011 |
| CN | 202920766 U | 5/2013 |
| CN | 203263987 U | 11/2013 |
| CN | 203694328 U | 7/2014 |
| CN | 203943990 U | 11/2014 |
| CN | 204017056 U | 12/2014 |
| CN | 204364609 U | 6/2015 |
| CN | 204864455 U | 12/2015 |
| CN | 204864460 U | 12/2015 |
| EP | 0 056 028 A1 | 7/1982 |
| EP | 0292432 B1 | 5/1991 |

OTHER PUBLICATIONS

International Search Report and the International Written Opinion of the Searching Authority dated May 1, 2017, in connection with corresponding international Application No. PCT/US2017/015234 filed Jan. 27, 2017 (11 pgs.).

Chinese Office Action dated Feb. 19, 2021, in connection with corresponding CN Application No. 201780008575.X (6 pp., including machine-generated English translation).

Chinese Search Report dated Feb. 4, 2021, in connection with corresponding CN Application No. 201780008575.X (6 pp., including machine-generated English translation).

Chinese Office Action dated Jun. 17, 2020, in connection with corresponding CN Application No. 201780008575.X (16 pgs., including machine-generated English translation).

Chinese Search Report dated Jun. 10, 2020, in connection with corresponding CN Application No. 201780008575.X (3 pgs.).

Communication Pursuant to Article 94(3) EPC dated May 10, 2022, in connection with corresponding European Application No. 17744932.9; 7 pages.

* cited by examiner

BREATHING MASK

PRIORITY CLAIM

This application claims priority as a continuation of U.S. patent application Ser. No. 15/416,224, filed on Jan. 26, 2017, entitled "BREATHING MASK," which claims priority to U.S. Provisional Patent Application No. 62/287,625, filed on Jan. 27, 2016, the entire contents of which are hereby incorporated by reference.

BACKGROUND

Critically ill patients suffering from a wide range of respiratory disturbances and cardiovascular failure often require noninvasive ventilatory support using a breathing mask (covering mouth and nose) such as a Bi-level Positive Airway Pressure mask to regulate normal respiratory patterns. With this noninvasive mask, the patient is able to speak, swallow and cough, and can avoid many complications due to endotracheal intubation. There are many forms of full face breathing masks currently available however these suffer from disadvantages such as lack of access for any form of nutrition support, discomfort in use and poor sealing when used in conjunction with a nasogastric tube. While wearing the breathing mask, patients are not able to have liquids or food, as access to the patient's mouth or nose is restricted due to the undesirability of or an inability to remove the mask. This can lead to nutritional deprivation. When patients are treated with a breathing mask, nutrition is often considered a secondary concern. It is estimated that 60% of critically chronic obstructive pulmonary disease patients with acute respiratory failure suffer from malnutrition. It has further been shown that proper nutrition can help to restore respiratory breathing strength. The current practice to address this issue is to insert a nasogastric tube and then restore the breathing mask. The nasogastric tube is retained between the mask and the patient's cheek subsequently creating a poor seal and air leakage. This results in removal of the nasogastric tube and cessation of nutrition support. Consequently, it is desirable to avoid sacrificing adequate nutrition for proper respiratory treatment. A breathing mask that accommodates the use of a nasogastric tube for enteral feeding while maintaining an airtight seal around the patient's face, may therefore be desired.

SUMMARY

According to an exemplary embodiment, a breathing mask may be provided. The breathing mask may include a frame capable of creating an airtight seal over a user's mouth and nose. The breathing mask may further include a breathing port capable of receiving a breathing tube. The breathing mask may also include a feeding tube port capable of receiving a feeding tube.

According to another exemplary embodiment, a breathing mask may include a frame configured to create an airtight seal over a user's mouth and nose, at least one breathing tube port disposed in the frame, and a feeding tube port disposed in the frame centrally above the breathing tube port. The breathing mask may further include a gripping element disposed on the frame centrally above the feeding tube port and capable of securing a feeding tube passing through the feeding tube port. The breathing mask may also include a feeding tube port sealing cap capable of sealing the feeding tube port.

According to yet another exemplary embodiment, a breathing mask may be provided. The breathing mask may include a frame having a breathing tube port and a nasogastric feeding tube rally installed therein. The breathing tube port and nasogastric feeding tube port may be vertically aligned along a central axis of the breathing mask. The feeding tube port may further include a locking element for securing a feeding tube passing through the feeding tube port, a sealing element for maintaining an airtight seal between the feeding tube port and the feeding tube, and a sealing cap capable of sealing the feeding tube port when not in use.

BRIEF DESCRIPTION OF THE FIGURES

Advantages of embodiments of the present invention will be apparent from the following detailed description of the exemplary embodiments. The following detailed description should be considered in conjunction with the accompanying figures in which.

Exemplary

Exemplary

Exemplary

Exemplary

Exemplary

Exemplary

Exemplary

Exemplary

Exemplary

Exemplary

Exemplary

Exemplary

Exemplary

DETAILED DESCRIPTION

Figure 1:
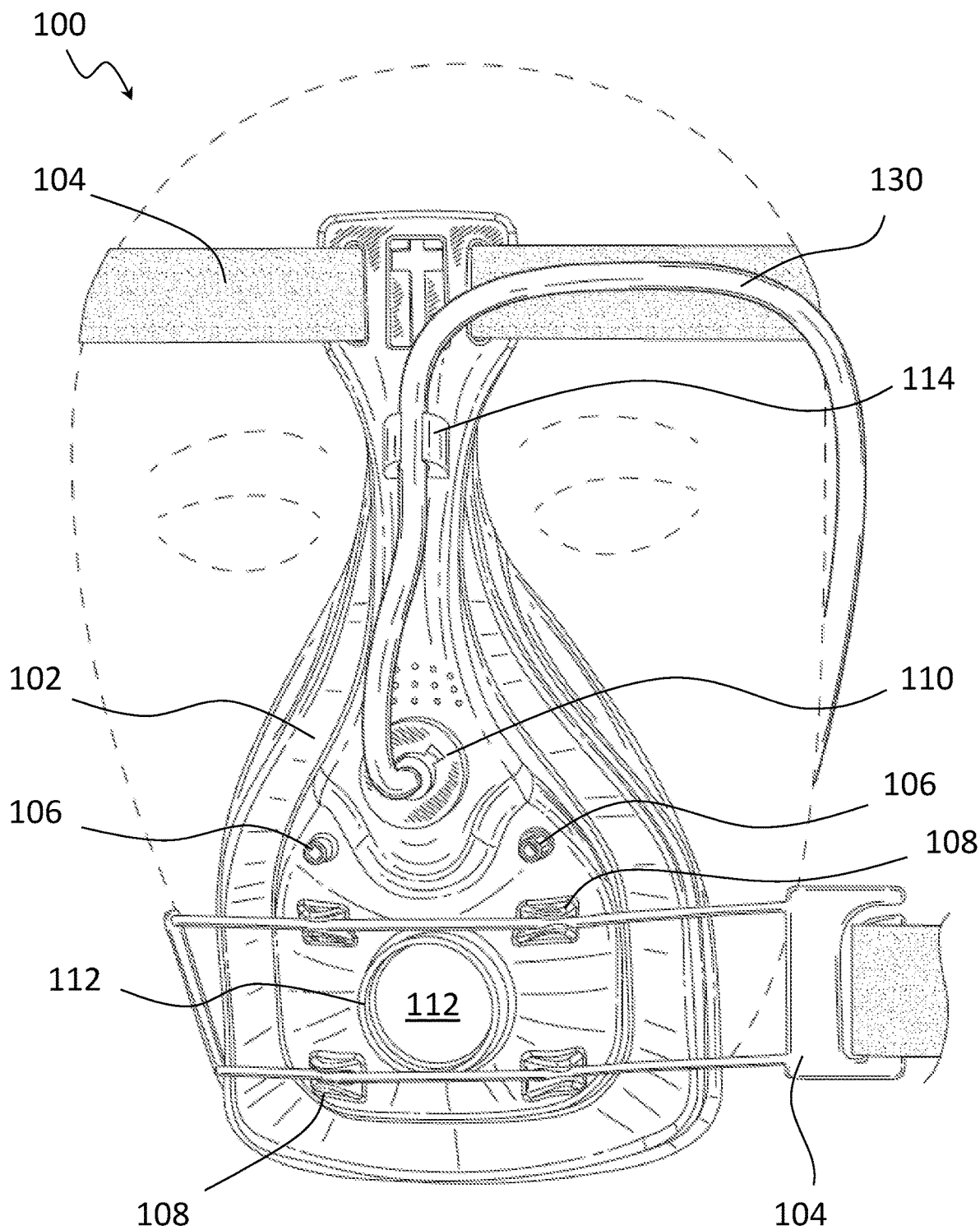
FIG. 1 shows a breathing mask with an enteral nutrition port.
Figure 2:
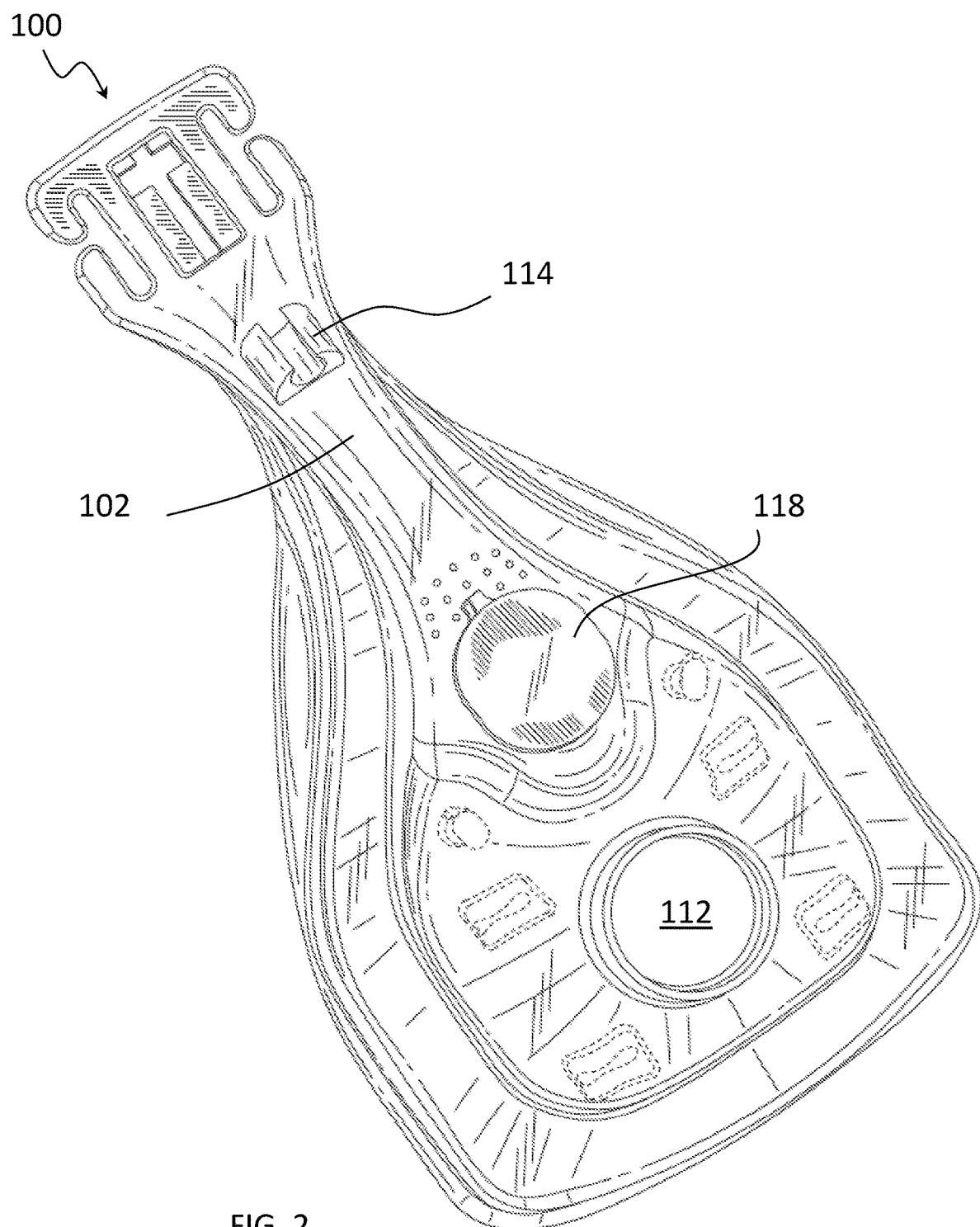
FIG. 2 shows a breathing mask with an enteral nutrition port.
Figure 3:
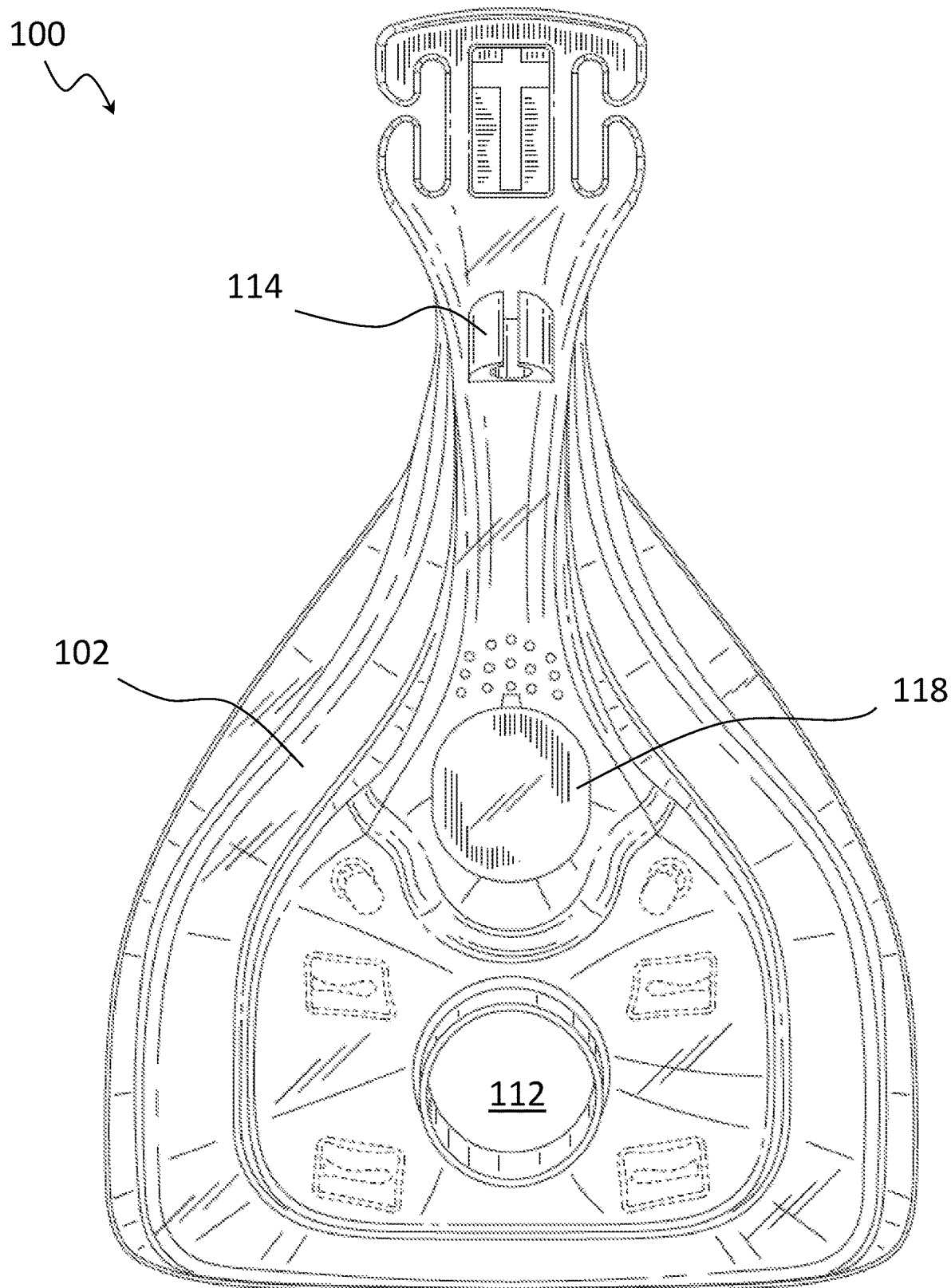
FIG. 3 shows a breathing mask with an enteral nutrition port.
Figure 4:
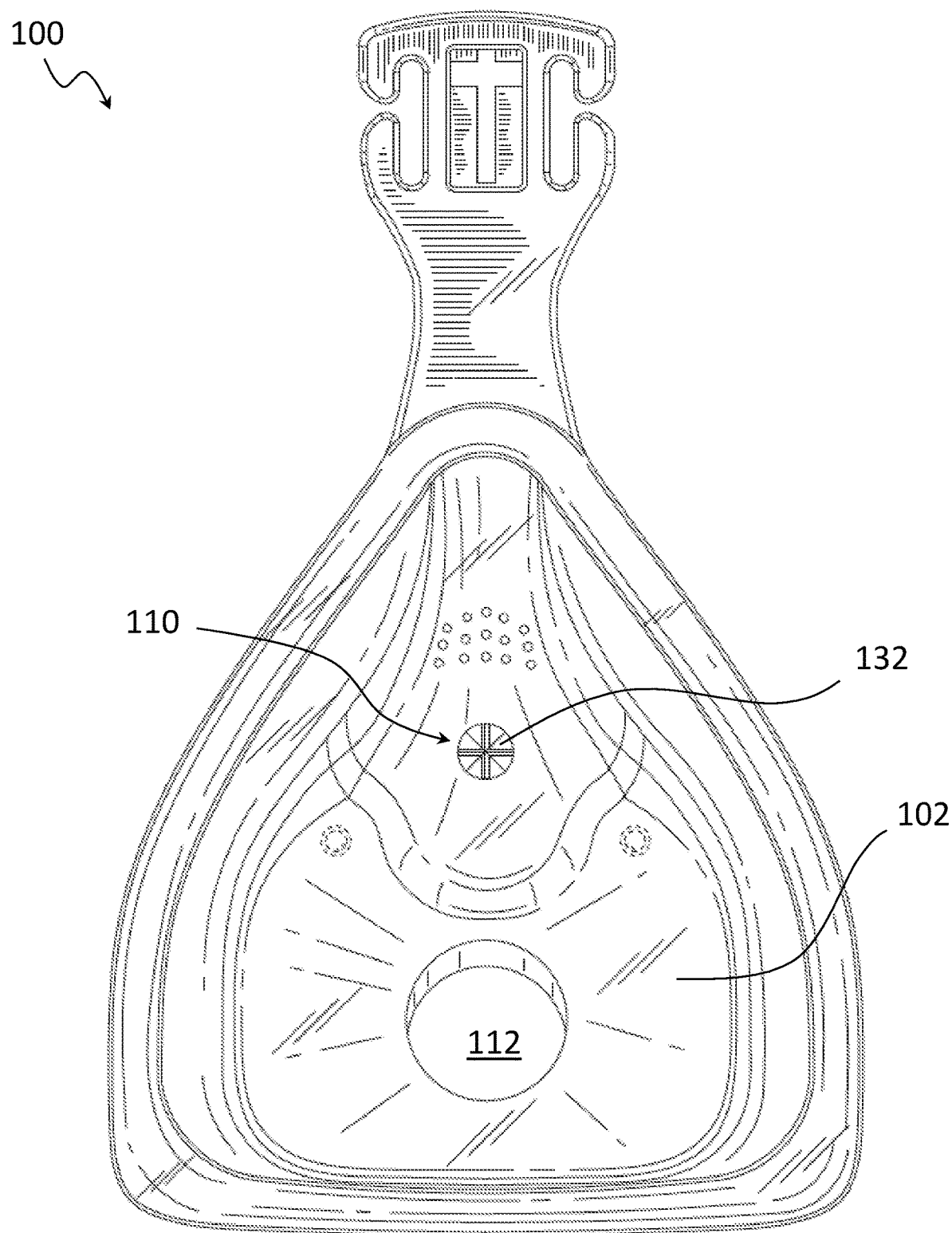
FIG. 4 shows a breathing mask with an enteral nutrition port.
Figure 5:
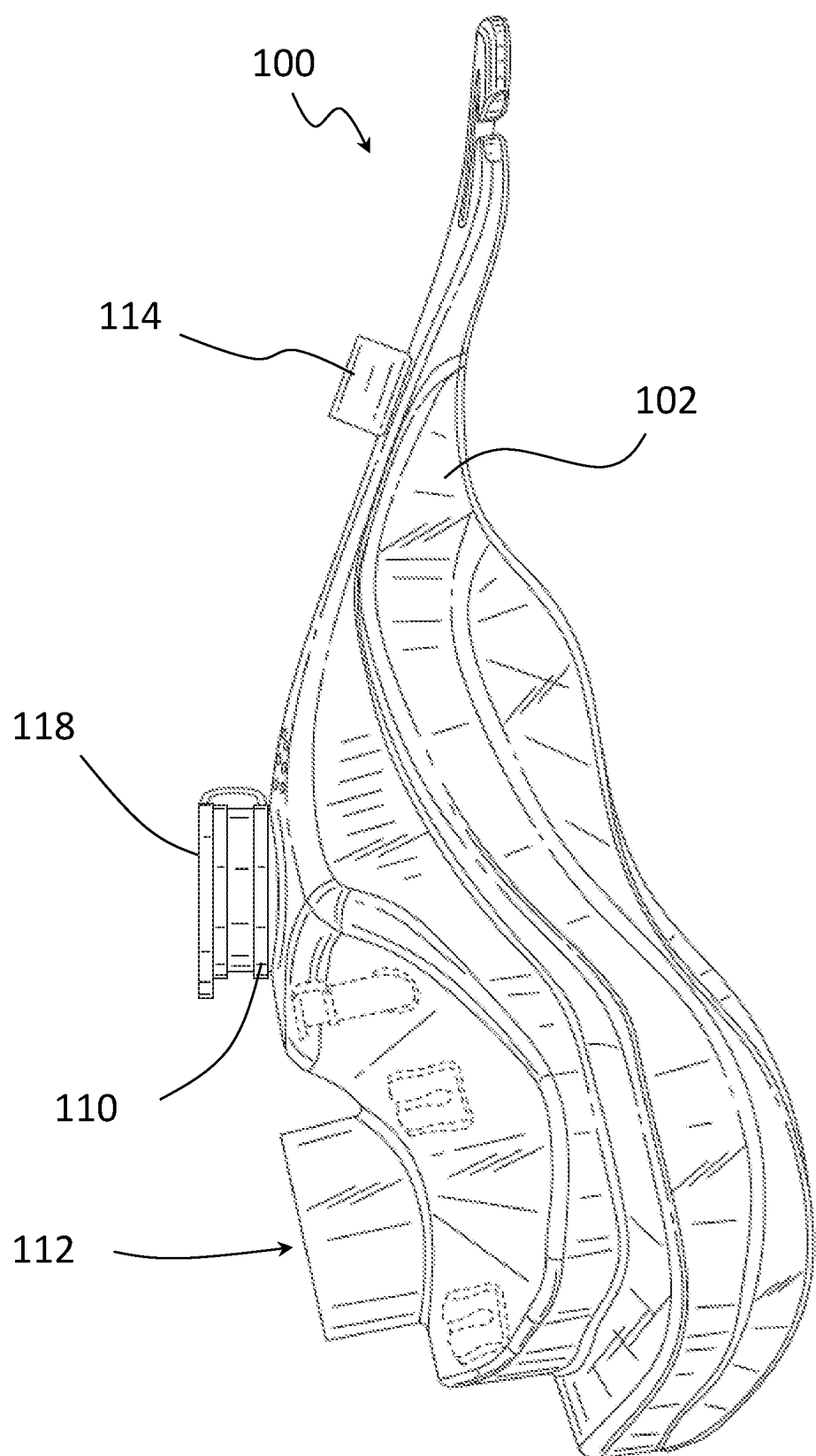
FIG. 5 shows a breathing mask with an enteral nutrition port.
Figure 6:
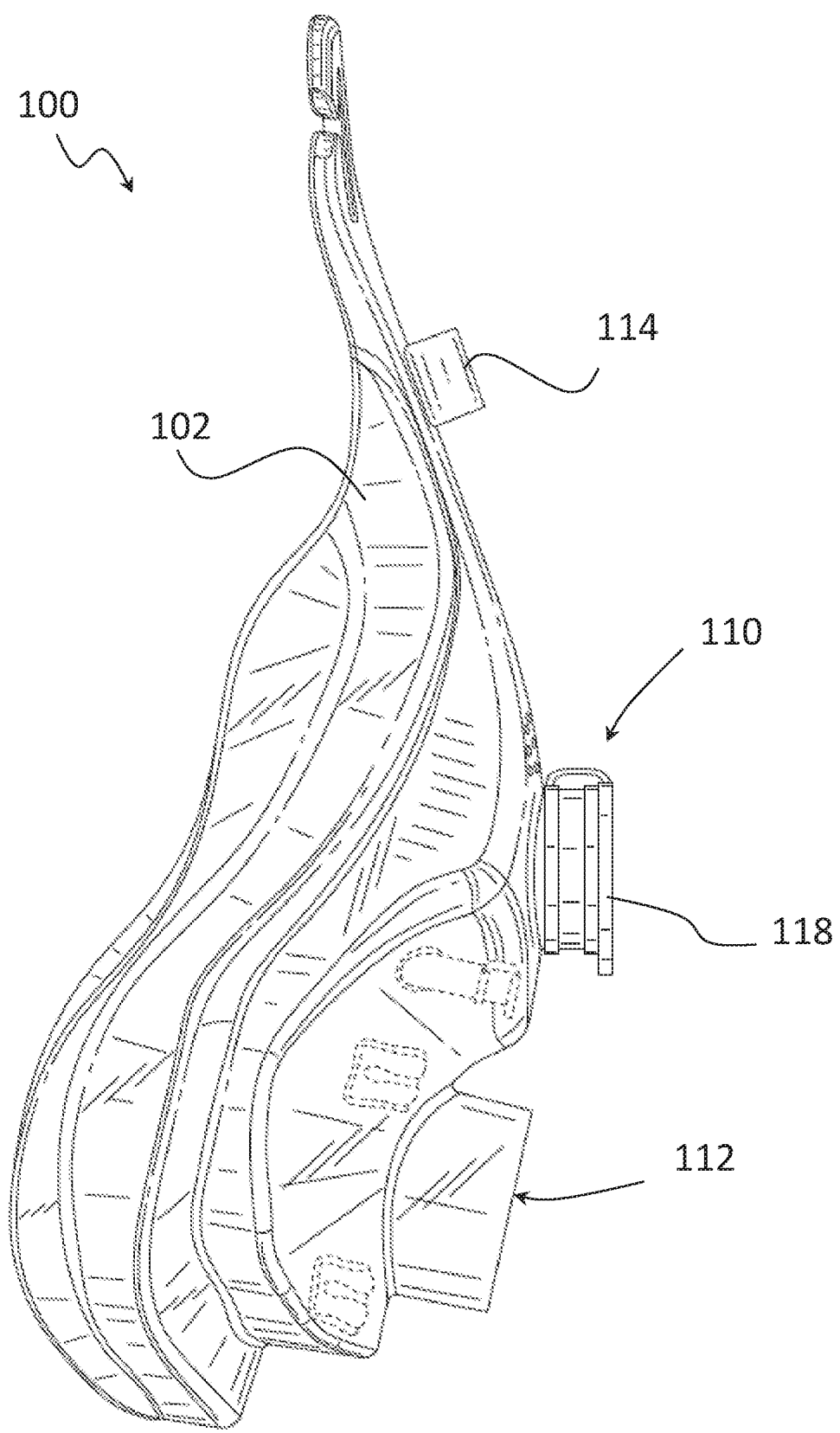
FIG. 6 shows a breathing mask with an enteral nutrition port.
Figure 7:
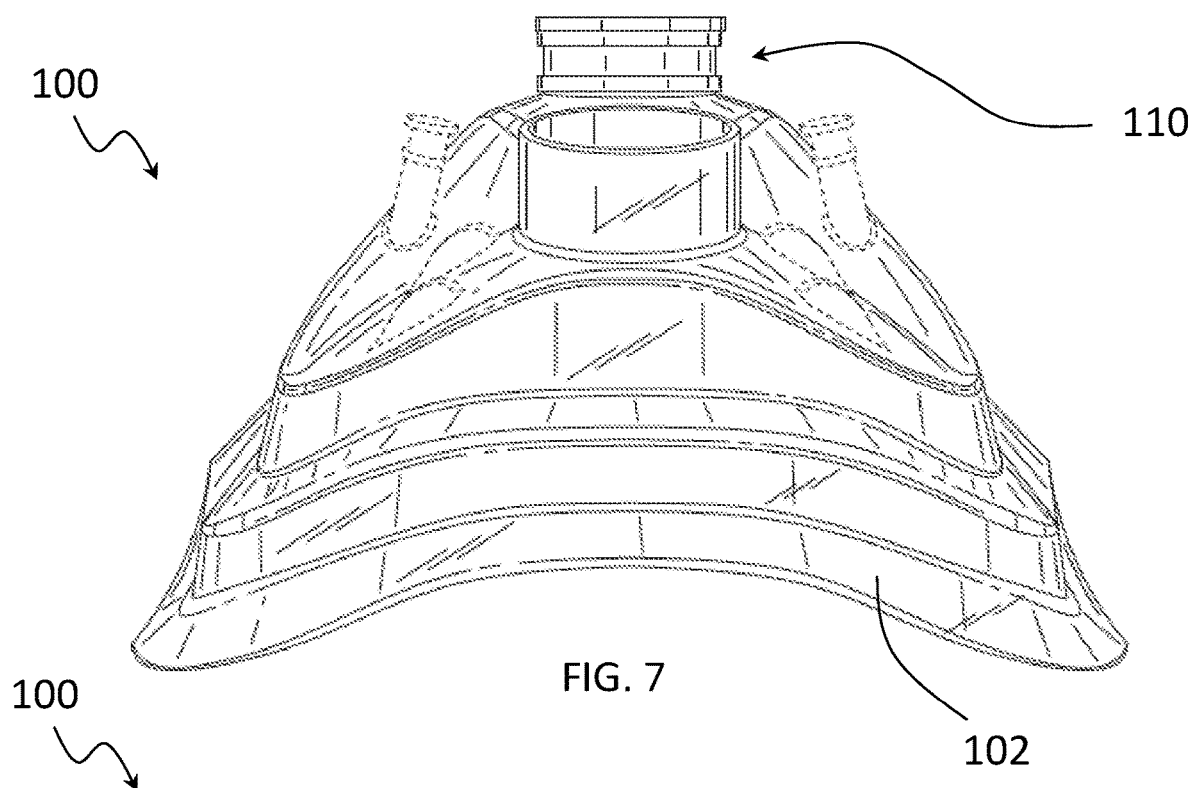
FIG. 7 shows a breathing mask with an enteral nutrition port.
Figure 8:
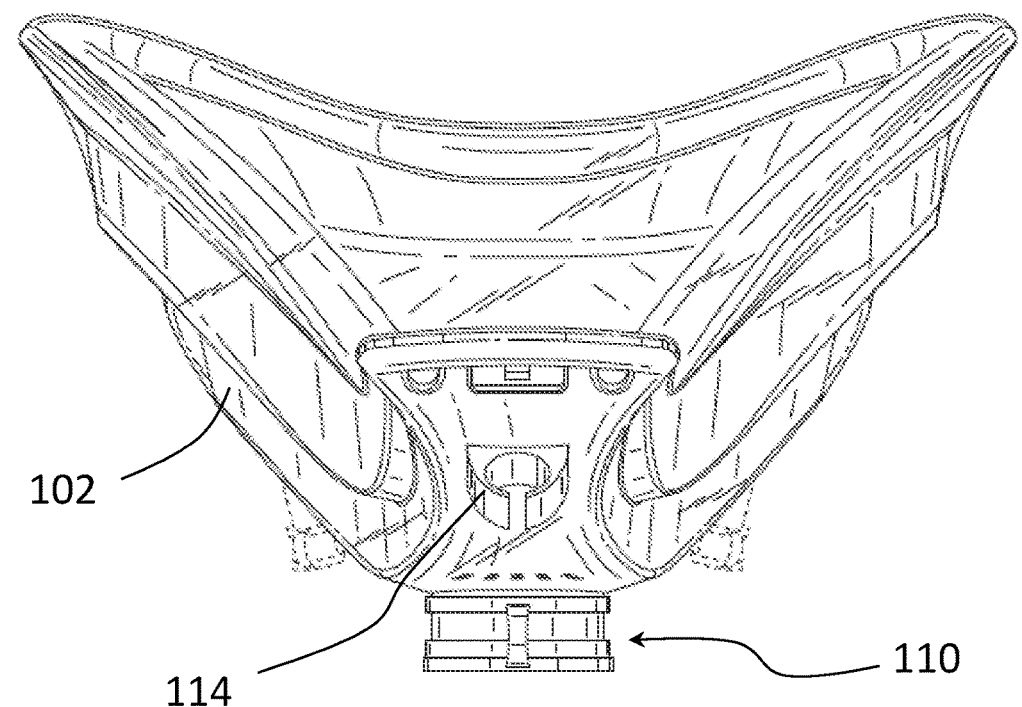
FIG. 8 shows a breathing mask with an enteral nutrition port.
Figure 9:
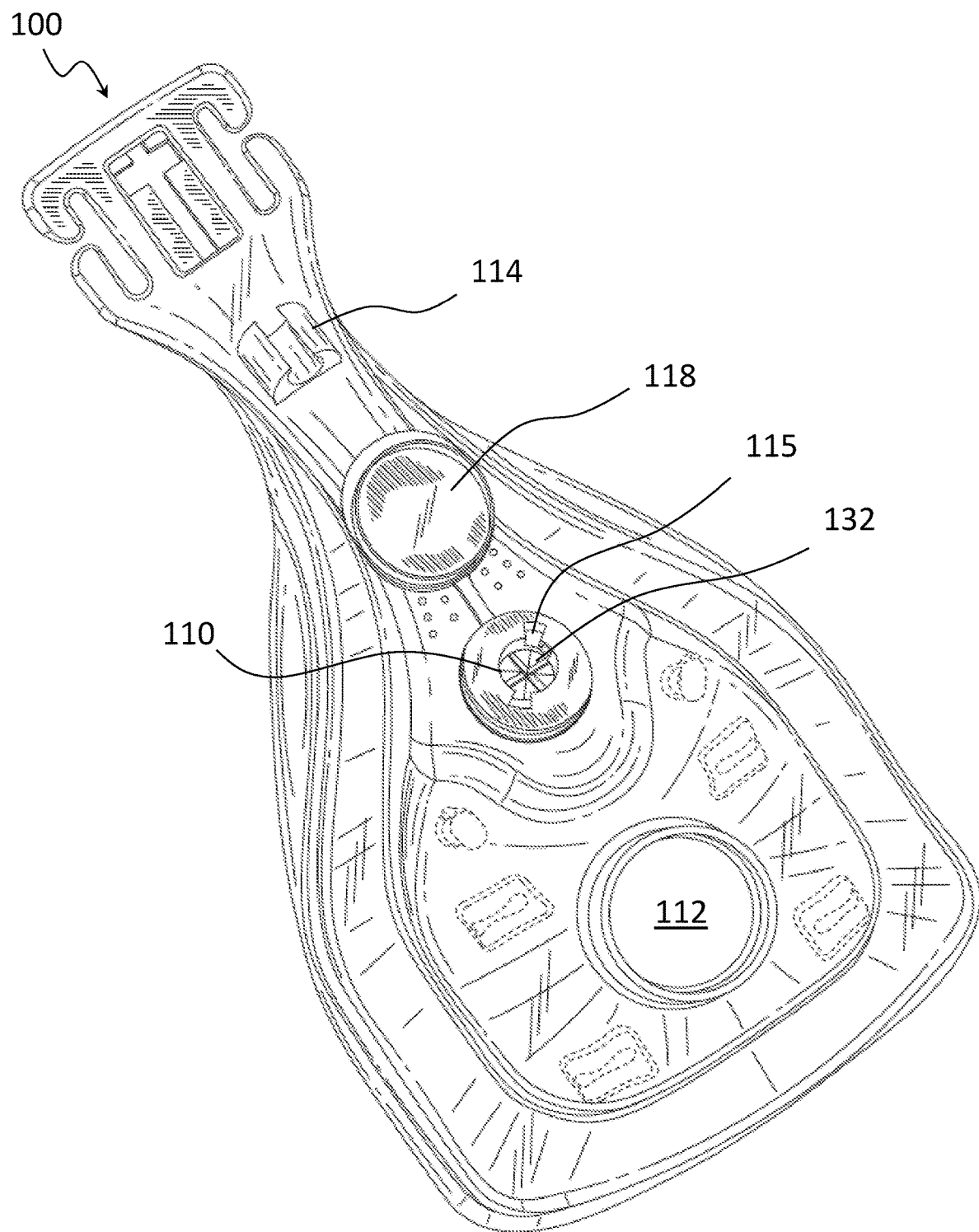
FIG. 9 shows a breathing mask with an enteral nutrition port.
Figure 10:
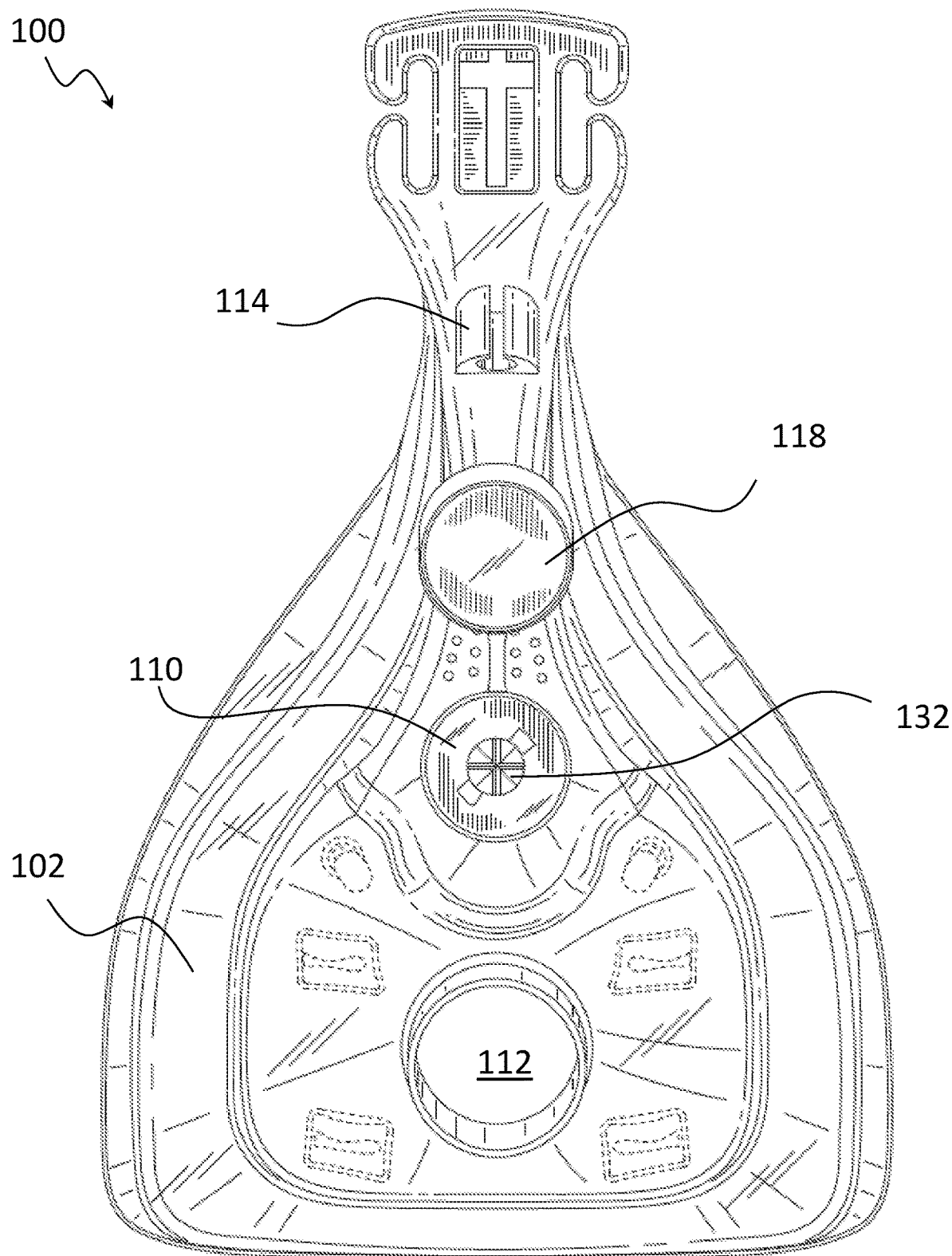
FIG. 10 shows a breathing mask with an enteral nutrition port.
Figure 11:
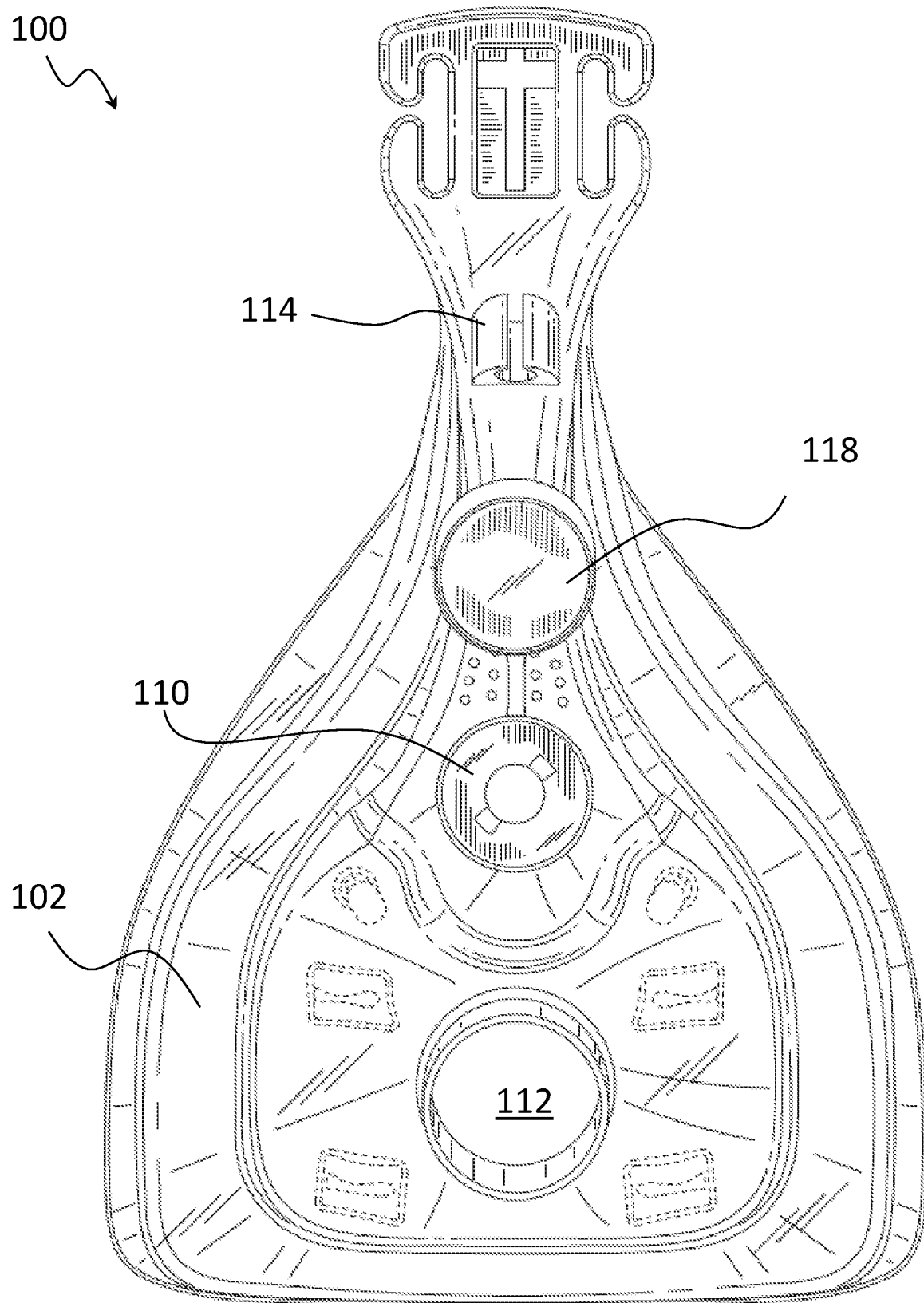
FIG. 11 shows a breathing mask with an enteral nutrition port.
Figure 12:
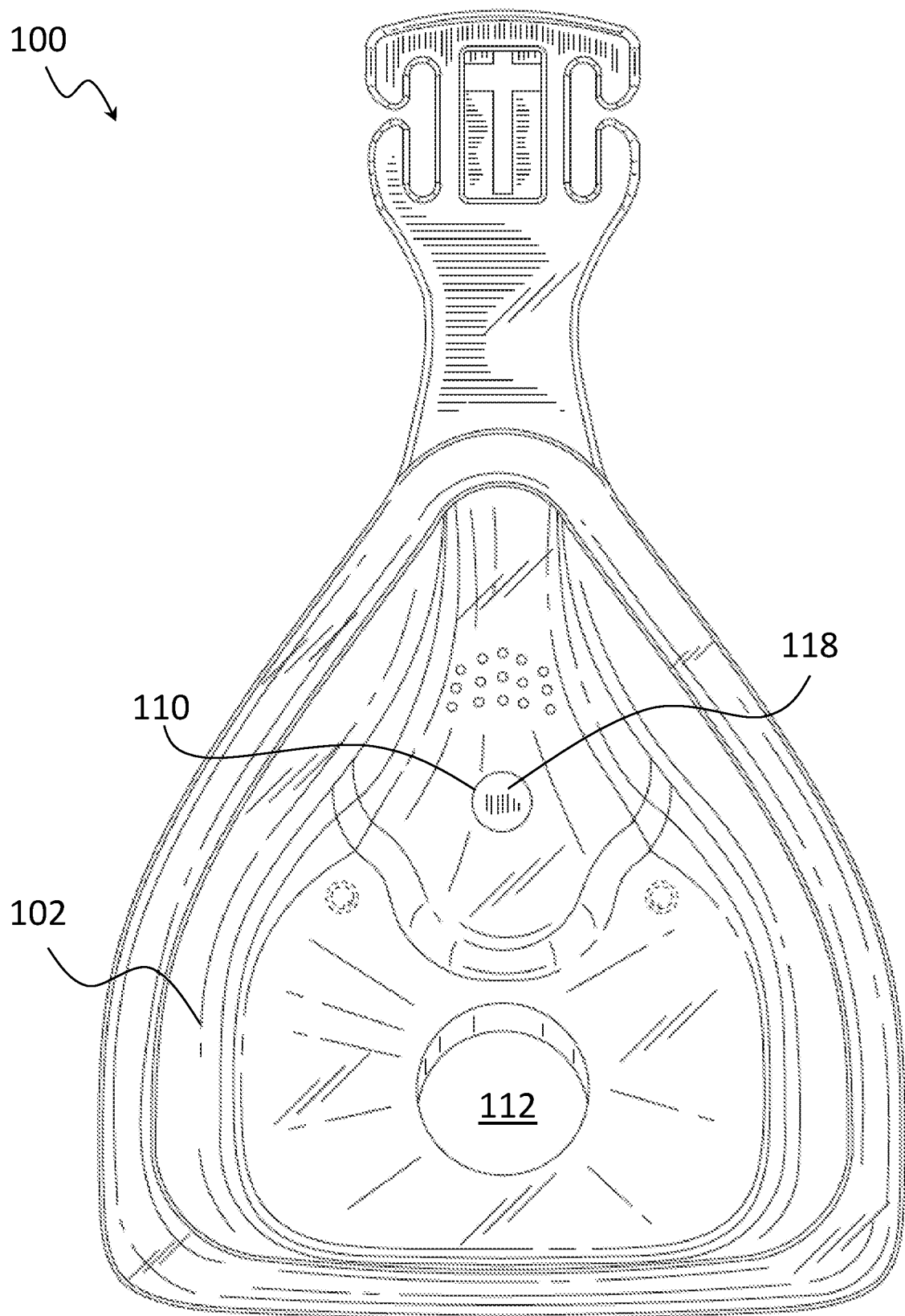
FIG. 12 shows a breathing mask with an enteral nutrition port.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

According to an exemplary embodiment, as shown in FIG. 1-13 generally, a breathing mask enteral nutrition nasogastric tube port (BENT-PORT) may be provided. A breathing mask 100 may include a breathing port 112 for accommodating an air tube providing the flow of a desired gas, such as oxygen, into the mask, as would be understood by a person having ordinary skill in the art. Breathing mask 100 may further include a feeding tube port 110. The port 110 may allow a nasogastric tube 130 to pass through the mask 100 without substantially affecting the seal or pressure of the mask, while accommodating enteral feeding. In an exemplary embodiment, a respiratory or breathing oral/nasal mask assembly 100 may include a frame 102, which may be capable of covering a user's nose or a user's nose and mouth, and headgear 104, which may secure the frame to the user's head. In addition to a breathing port 112 and feeding tube port 110, mask 100 may further include at least one auxiliary or supplemental port 106. Auxiliary or supplemental port 106 may allow for introducing, sampling, monitoring, or extracting gases or other substances from within a breathing mask. Breathing mask assembly 100 may be an oronasal mask, full face mask, or nasal mask. Headgear 104 may include at least one strap. Headgear 104 may further include a frame, which may be secured to mask 100 by at least one headgear securing grip 108. In addition to a breathing port, the mask assembly may further include a cushion, which may create a seal between the mask and the user. The cushion may additionally provide comfort to the user. A mask assembly may further include inserts with nasal cushions and forehead pads. A nose bridge of mask 100 may optionally be soft in order to prevent skin breakdown. The frame 102 may be made of a variety of materials including, but not limited to, silicone, plastic, rubber, or polymers, as would be understood by a person having ordinary skill in the art. The frame 102 may be substantially rigid. The frame 102 may optionally be transparent.

Breathing mask 100 may further include a tube port 110. Port 110 may accommodate a feeding tube, such as a nasogastric (NG) tube, a nasoduodenal (ND) tube, a nasojejunal (NJ) tube, or other feeding tubes as would be understood by a person having ordinary skill in the art. Port 110 may allow for enteral feeding and breathing of patients simultaneously. Port 110 may be applicable for breathing masks used by humans and animals. Port 110 may be multi-functional. For example, port 110 may be used for nutritional use, to provide water, to provide other liquids, or to provide medications, including crushed medications, to humans or animals that require a breathing mask. In at least one exemplary embodiment, port 110 may allow for the use of a nasogastric tube 130 without disrupting the seal of a breathing mask. The mask 100 and port 110 may be composed of the same material or may be different materials. In an exemplary embodiment, at least one of the mask 100 and port 110 may optionally be transparent or opaque. According to some exemplary embodiments, port 110 may be disposed centrally on mask 100 above a breathing tube port 112 in order for a feeding tube to be comfortably inserted into either nostril of a user.

In an exemplary embodiment, the breathing mask 100 may be a Bi-Level Positive Air Pressure (BiPAP) Mask and may be capable of accommodating a Nasogastric (NG) Tube 130 through the port 110. The breathing mask 100 with the port may maintain the functionality of BiPAP by achieving internal pressure within approximately 5% of a standard BiPAP mask. The port 110 may also be compatible with Continuous Positive Airway Pressure (CPAP) masks, and other similar masks as would be understood by a person having ordinary skill in the art. Additionally, the NG tube 130 may be secured to the mask 100 to limit movement of the tube when the length of tube 130 outside the mask is manipulated. Further to limiting undesired movement of the NG tube 130, the port 110 may be positioned in the mask 100 to comfortably, position an NG tube 130 for a patient, when inserted.

In an exemplary embodiment, as shown in FIG. 1-12, the port 110 may be located above a breathing tube port or air tubing port 112, along a vertical axis of a breathing mask 100. In alternative exemplary embodiments, the port 110 may be located in any desired location on breathing mask 100. In some exemplary embodiments, multiple ports 110 may be provided to allow insertion of an NG tube 130 in a variety of orientations or to allow for insertion of multiple NG tubes, or other desired tubes as may be understood by a person having ordinary skill in the art. The at least one port 110 may be provided aerially or on top of the mask to maintain the airtight seal between the breathing mask 100 and a user's head.

In at least some exemplary embodiments, as shown in FIGS. 1-13, the breathing mask 100 may further include a tube gripping element 114. Gripping element 114 may removably secure a tube 130 to the mask in a desired orientation and may limit undesired motion of the tube during use. In some embodiments, gripping element 114 may be positioned above the port 110 along a vertical axis. In other exemplary embodiments, gripping element 114 may be located in any desired location on breathing mask 100. In yet further exemplary embodiments, multiple gripping elements 114 may be included on breathing mask 100 to allow for multiple desired orientations of an NG tube.

Port 110 may optionally incorporate a variety of sealing elements for engaging a tube 130. Sealing elements may include a port locking element 115 and corresponding tube locking element 116 disposed along the length of tube 130. For example, port 110 may include a one-way valve, a Luer-lock, a cross-slit valve, a seam port, a plug, or other similar port types as would be understood by a person having ordinary skill in the art. In some exemplary embodiments, optional port locking element 115 and corresponding tube locking element 116 may form a screw-type connection or other male-female connection as would be understood by a person having ordinary skill in the art. In yet further embodiments, multiple sealing elements may be incorporated. For example, port 110 may include a port locking element 115 for engaging a corresponding tube locking element 116 on tube 130 in addition to a cross-slit valve 132 for added sealing around tube 130 when disposed through port 110.

Locking elements 115, 116 may lock the position and orientation of tube 130 in relation to port 110 in addition to providing a seal between port 110 and tube 130. Cross-slit valve 132 or alternative sealing elements may provide additional air sealing at port 110. Creating a substantially air tight seal at port 110 may maintain the integrity of the full face breathing mask.

In some embodiments, a sealing cap 118 may be provided for sealing the port when a tube is not inserted. This may maintain the seal and pressure achieved by the mask. Sealing cap 118 may be capable of engaging the desired port type, as would be understood by a person having ordinary skill in the art. Sealing cap 118 may optionally be tethered to the mask to prevent misplacement. In yet further embodiments, sealing cap 118 may be a plug or solid tube locking element 116, as discussed below, capable of preventing airflow as would be understood by a person having ordinary skill in the art.

Figure 13:
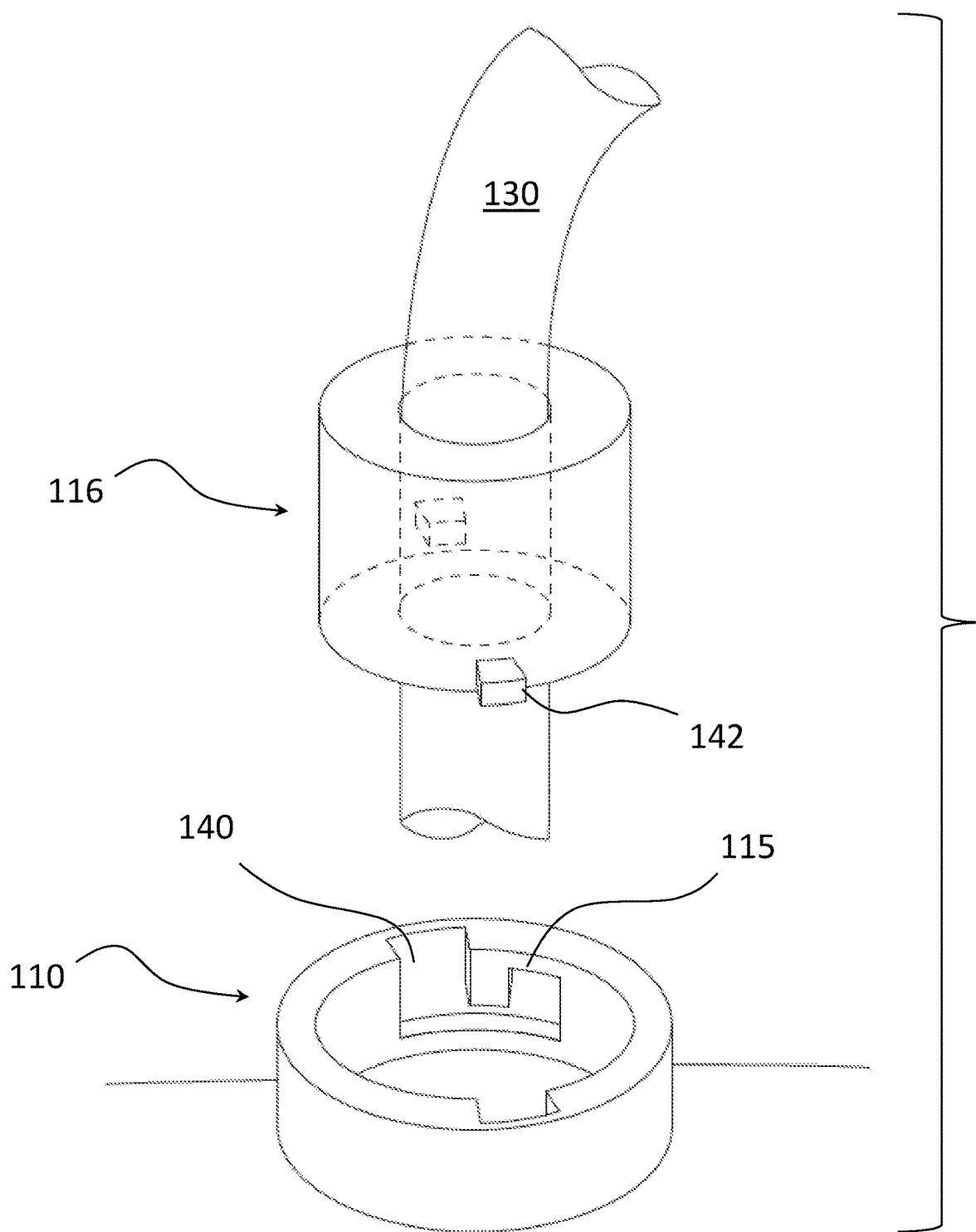
FIG. 13 shows a enteral nutrition port locking mechanism.

The locking elements of an exemplary embodiment may be in FIG. 13. A port locking element 115 may have at least one female connection portion or track 140 and may be disposed on the inner surface of port 110. A tube locking element 116, may be a sleeve capable of passing over tube 130 having at least one corresponding male connection portion 142 for engaging track 140. Tube locking element 116 may be positioned at a desired location along the length of a tube 130. Tube locking element 116 may fit tightly around tube 130, maintaining an airtight seal. In an exemplary embodiment, tube locking element 116 may include at least one slit or seam to facilitate adjustment along the length of tube 130. The at least one slit or seam may extend partially the length of tube locking element 116 and when flexed may adjust the fit around tube 130 to facilitate sliding the tube 130 through tube locking element 116. When engaged with port locking element 115, tube locking element 116 may prevent tube 130 from being dislodged or moving in an undesired manner.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined following claims.

What is claimed is:

1. A breathing mask comprising:
   a frame, wherein the frame has a top edge and a bottom edge, which are configured to align respectively with a top and bottom of a user's face;
   a breathing port;
   an enteral nutrition port disposed in the frame vertically aligned with the breathing port, between the breathing port and the top edge, and configured to receive an enteral nutrition tube;
   a tube grip disposed on an outer surface of the frame between the enteral nutrition port and the top edge, wherein the tube grip is configured to secure the enteral nutrition tube in an orientation along a vertical axis from the top edge to the enteral nutrition port;
   a port lock disposed in the enteral nutrition port; and
   an enteral nutrition tube lock disposed on the enteral nutrition tube, wherein the port lock is configured to secure the enteral nutrition tube lock in the enteral nutrition port and lock a position and orientation of the enteral nutrition tube in relation to the enteral nutrition port.

2. The breathing mask of claim 1, wherein the enteral nutrition port is an oral feeding tube port.

3. The breathing mask of claim 1, wherein the enteral nutrition port is a nasal feeding tube port.

4. The breathing mask of claim 1, further comprising an enteral nutrition port sealing cap.

5. The breathing mask of claim 1, wherein the frame is configured to create an air-tight seal over the user's nose and mouth.

6. The breathing mask of claim 1, further comprising an enteral nutrition port valve disposed within an opening of the enteral nutrition port, wherein the port valve is configured to maintain a seal.

7. The breathing mask of claim 1, wherein the frame is transparent.

8. The breathing mask of claim 1, further comprising a cushion.

9. The breathing mask of claim 1, further comprising at least one auxiliary port.

10. The breathing mask of claim 9, the at least one auxiliary port comprises a first auxiliary port disposed between the enteral nutrition port and a left edge of the frame and a second auxiliary port disposed between the enteral nutrition port and a right edge of the frame.

11. The breathing mask of claim 1, wherein the enteral nutrition port and the breathing port are configured to provide simultaneous use of a breathing tube and the enteral nutrition tube.

12. The breathing mask of claim 1, wherein the enteral nutrition tube is an enteral feeding tube.

13. An enteral nutrition apparatus comprising:
   a mask configured to cover at least one of a user's mouth and nose;
   an enteral nutrition port disposed in the mask; and
   an enteral nutrition port sealing valve disposed within an opening of the enteral nutrition port, wherein the enteral nutrition port sealing valve is configured to maintain a seal,
   a tube grip disposed between the enteral nutrition port and a top edge, wherein the tube grip is configured to secure an enteral nutrition tube in an orientation along a vertical axis from the top edge to the enteral nutrition port;
   the enteral nutrition tube configured to pass through the enteral nutrition port; and
   an enteral nutrition port lock disposed in the enteral nutrition port and an enteral nutrition tube lock disposed on the enteral nutrition tube, wherein the enteral nutrition tube lock is configured to securely engage the enteral nutrition port lock and lock a position and orientation of the enteral nutrition tube in relation to the enteral nutrition port.

14. The enteral nutrition apparatus of claim 13, further comprising a breathing port disposed in the mask.

15. The enteral nutrition apparatus of claim 13, further comprising an enteral nutrition port cap configured to cover the enteral nutrition port.

16. A breathing mask comprising:
   a frame, wherein the frame has a top edge and a bottom edge, which are configured to align respectively with a top and bottom of a user's face;
   a breathing port;
   an enteral nutrition port disposed in the frame vertically aligned with the breathing port, between the breathing port and the top edge, and configured to receive an enteral nutrition tube;
   a tube grip disposed on an outer surface of the frame between the enteral nutrition port and the top edge, wherein the tube grip is configured to secure the enteral nutrition tube in an orientation along a vertical axis from the top edge to the enteral nutrition port;
   an enteral nutrition port valve disposed within an opening of the enteral nutrition port, wherein the port valve is configured to maintain a seal;
   an enteral nutrition tube lock disposed on the enteral nutrition tube; and a port lock configured to secure the enteral nutrition tube lock in the enteral nutrition port.

\* \* \* \* \*